(12) United States Patent
Klatzmann et al.

(10) Patent No.: US 12,403,181 B2
(45) Date of Patent: Sep. 2, 2025

(54) COMBINATION OF INTERLEUKIN-2 WITH AN INTERLEUKIN 1 INHIBITOR, CONJUGATES AND THERAPEUTIC USES THEREOF

(71) Applicants: ILTOO PHARMA, Paris (FR); SORBONNE UNIVERSITE, Paris (FR); ASSISTANCE PUBLIQUE—HÔPITAUX DE PARIS, Paris (FR); INSERM (INSTITUT NATIONAL DE LA SANTÉ ET DE LA RECHERCHE MÉDICALE), Paris (FR)

(72) Inventors: David Klatzmann, Paris (FR); Jérémie Mariau, Fontenay-sous-Bois (FR); Paul-Gydéon Ritvo, Paris (FR); Encarnita Mariotti-Ferrandiz, Paris (FR); Thomas Vazquez, Montreuil (FR); Nicolas Billiald, Paris (FR)

(73) Assignees: ILTOO PHARMA, Paris (FR); SORBONNE UNIVERSITE, Paris (FR); ASSISTANCE PUBLIQUE—HÔPITAUX DE PARIS, Paris (FR); INSERM (INSTITUT NATIONAL DE LA SANTÉ ET DE LA, Paris (FR); RECHERCHE MÉDICALE), Paris (FR)

( * ) Notice: Subject to any disclaimer, the term of this patent is extended or adjusted under 35 U.S.C. 154(b) by 1075 days.

(21) Appl. No.: 17/268,030

(22) PCT Filed: Aug. 13, 2019

(86) PCT No.: PCT/EP2019/071684
§ 371 (c)(1),
(2) Date: Feb. 11, 2021

(87) PCT Pub. No.: WO2020/035482
PCT Pub. Date: Feb. 20, 2020

(65) Prior Publication Data
US 2021/0236599 A1  Aug. 5, 2021

(30) Foreign Application Priority Data
Aug. 13, 2018 (EP) .................... 18306112

(51) Int. Cl.
| | |
|---|---|
| *A61K 38/20* | (2006.01) |
| *A61K 38/17* | (2006.01) |
| *A61K 47/62* | (2017.01) |
| *C07K 16/24* | (2006.01) |

(52) U.S. Cl.
CPC ........ *A61K 38/2013* (2013.01); *A61K 38/177* (2013.01); *A61K 47/62* (2017.08); *C07K 16/245* (2013.01)

(58) Field of Classification Search
CPC .................................................. A61K 38/2013
See application file for complete search history.

(56) References Cited

U.S. PATENT DOCUMENTS

2002/0077294 A1  6/2002  Kay et al.
2017/0173117 A1  6/2017  Paulsen et al.

OTHER PUBLICATIONS

Ali, A. M., et al. "A proposed biology-and biomarker-based algorithm for management of acute GvHD" Bone Marrow Transplantation, vol. 52, No. 2, pp. 337-340, Feb. 2017.
Chiron, Proleukin (aldesleukin) for injection prescribing information (United States), Chiron, Annruel Studio Graphics, Scarborough, ME, US, Jan. 1, 1998.
Smaldini, Paolo L., et al. "Systemic IL-2/anti-IL-2Ab complex combined with sublingual immunotherapy suppresses experimental food allergy in mice through induction of mucosal regulatory T cells" Allergy, vol. 73, No. 4, pp. 885-895, Apr. 1, 2018.
Vazquez-Lombardi, Rodrigo, et al. "Molecular engineering of therapeutic cytokines" Antibodies, vol. 2, No. 3, pp. 426-451, Sep. 2013.

*Primary Examiner* — Prema M Mertz
(74) *Attorney, Agent, or Firm* — Mintz Levin Cohn Ferris Glovsky and Popeo, P.C.

(57) ABSTRACT

The present invention relates to a combination of i) interleukin-2 (IL-2) and ii) an interleukin 1 (IL-1) inhibitor, for use in treating an auto-immune and/or inflammatory disorder in a subject. It is also provided a pharmaceutical composition comprising interleukin-2 (IL-2) and an interleukin-1 (IL-1) inhibitor. The invention further provides a conjugate comprising IL-2 conjugated to an IL-1 inhibitor.

17 Claims, 4 Drawing Sheets

Specification includes a Sequence Listing.

COMBINATION OF INTERLEUKIN-2 WITH AN INTERLEUKIN 1 INHIBITOR, CONJUGATES AND THERAPEUTIC USES THEREOF

RELATED APPLICATIONS

This application is a United States National Phase under 35 U.S.C. § 371 of International Application No. PCT/EP2019/071684 filed on Aug. 13, 2019, which claims the benefit of, and priority to, European Patent Application No. 18306112.6 filed on Aug. 13, 2018, both of which are incorporated by reference herein in their entirety for all purposes.

SEQUENCE LISTING

The application contains a Sequence Listing that has been filed electronically in the form of a text file, created Aug. 13, 2019, and named "B2816PC00_SEQUENCE-LISTING.txt" (2,737 bytes), the contents of which are incorporated by reference herein in their entirety.

The present invention relates to combination products and conjugates for use in treating an auto-immune and/or inflammatory disorder

BACKGROUND OF THE INVENTION

Regulatory T cells (Treg) play a crucial role in maintaining immune homeostasis since Treg dysfunction in both animals and humans is associated with multi-organ autoimmune and inflammatory diseases. While IL-2 is generally considered to promote T-cell proliferation and enhance effector T-cell function, recent studies have demonstrated that treatments that utilize low-dose IL-2 unexpectedly induce immune tolerance and promote Treg development resulting in the suppression of unwanted immune responses (Klatzmann D, Abbas A K. Nat Rev Immunol. 2015 May; 15(5):283-94).

Autoimmune or inflammatory disorders involve both uncontrolled auto-antibody production and complex cellular responses.

To better understand the consequences of an IL-2 treatment, and because follicular regulatory T (Tfr) cells are thought to derive from Treg cells, Ritvo et al, (Sci Immunol. 2017 Sep. 8; 2(15)) assessed Tfr cell response to IL-2. They found that Tfr cell proportion was reduced rather than augmented during IL-2 treatment. Ritvo et al (supra) identified these cells as a rare population of CD4+CXCR5+PD-1+Foxp3+ cells that do not express CD25 and thus do not respond to interleukin-2. Because CD25 was thought to be expressed on Tfr cells (Maceiras et al, Immunology, 152, 25-35, 2017), many if not most studies of Tfr function were performed with mixture of Tfr cell and Tregs (Ritvo et al. supra). The stringent identification of Tfr cells as CD25 negative allowed to study their gene expression pattern. This revealed the previously missed expression of decoy molecules for the interleukin-1 signaling pathway by these cells. This observation was further confirmed by immunophenotyping experiments (Ritvo et al, supra). Furthermore, Ritvo et al. (supra) then showed that the IL-1 signaling pathway was involved in the positive regulation of antibody response by Tfh cells and in the negative regulation of these responses by Tfr cells. However, the mechanisms at work were not fully understood, and notably whether these effects were direct or indirect.

There is still a need to provide global therapies of autoimmune or inflammatory disorders which would act on both cellular and humoral immune responses.

SUMMARY OF THE INVENTION

The invention provides a combination of i) interleukin-2 (IL-2) and ii) an interleukin 1 (IL-1) inhibitor, for use in treating an auto-immune and/or inflammatory disorder in a subject.

Such combination makes it possible to provide a global action on such disorders: while IL-2 increases the Treg cells, hence controlling the cell responses, the IL-1 inhibitor reinforces the action of IL-2 on the humoral response, and both treatments altogether reduce inflammation.

In a preferred embodiment the IL-1 inhibitor is selected from the group consisting of i) a soluble form of an IL-1 receptor, ii) an anti-IL-1R antibody or a fragment thereof, and iii) an anti-IL-1 antibody or a fragment thereof.

Preferably the IL-1 inhibitor is a recombinant IL-1Ralpha, preferably anakinra.

In another particular embodiment, the IL-1 inhibitor is a soluble decoy IL-1 receptor, preferably rilonacept.

In still another particular embodiment, the IL-1 inhibitor is a neutralizing anti-IL-1alpha antibody, preferably canakinumab.

IL-2 can be administered sequentially or simultaneously with the IL-1 inhibitor.

Preferably IL-2 and the IL-1 inhibitor are to be administered within the same composition.

Another subject of the invention is thus a pharmaceutical composition comprising IL-2 and an IL-1 inhibitor.

It is further provided a kit comprising:
a. a container that contains IL-2; and
b. another container that contains an IL-1 inhibitor.

In a preferred embodiment, IL-2 is to be administered at a dose of 3.5 MIU/day or less, preferably at a dose of about 0.5 to 1.5 MIU/day.

Preferably the IL-1 inhibitor is to be administered intravenously or subcutaneously.

Preferably the IL-2 is administered subcutaneously.

In a preferred embodiment, both IL-2 and the IL-1 inhibitor are to be administered subcutaneously.

In a particular embodiment, the treatment comprises at least a first course wherein interleukin-2 is administered once per day during at least 3 consecutive days, followed by a maintenance treatment after 1 to 4 weeks.

Preferably IL-2 is administered repeatedly.

The present invention further provides a conjugate comprising IL-2 conjugated to an IL-1 inhibitor.

Such conjugate is also useful in treating an auto-immune and/or inflammatory disorder in a subject.

Preferably the combination or conjugate is administered repeatedly.

DETAILED DESCRIPTION OF THE INVENTION

Definitions

The "subject" or "patient" to be treated may be any mammal, preferably a human being. The human subject may be a child, an adult or an elder.

The term "treating" or "treatment" means any improvement in the disease. It includes alleviating at least one symptom, or reducing the severity or the development of the disease. In particular it includes reducing the risk, occurrence or severity of acute episodes (flares). The term "treating" or "treatment" encompasses reducing the progression of the disease. In particular the invention encompasses preventing or slowing down the progression of the disease. The term "treating" or "treatment" further encompasses prophylactic treatment, by reducing the risk or delaying the onset of the disease, especially in a subject who is asymptomatic but has been diagnosed as being "at risk".

"Regulatory T cells" or "Tregs" are T lymphocytes having immunosuppressive activity. Natural Tregs are characterized as CD4+CD25+Foxp3+ cells. Tregs play a major role in the control of inflammatory diseases, although their mode of action in such disease is not well understood. In fact, in most inflammatory diseases, Treg depletion exacerbates disease while Treg addition decreases it. Most Tregs are CD4+ cells, although there also exists a rare population of CD8+ Foxp3+ T lymphocytes with a suppressive activity.

Within the context of this application, "effector T cells" (or "Teff") designates conventional T lymphocytes other than Tregs (sometimes also referred to as Tconv in the literature), which express one or more T cell receptor (TCR) and perform effector functions (e.g., cytotoxic activity, cytokine secretion, etc). Major populations of human Teff according to this invention include CD4+ T helper lymphocytes (e.g., Th0, Th1, Th2, Th9, Th17, Tfh) and CD4+ or CD8+cytotoxic T lymphocytes, and they can be specific for self or non-self antigens.

Within the context of this application, "T follicular helper cells" (or "Tfh") designates T CD4+ lymphocytes that express BcL6, CXCR5 and PD1, are Foxp3−, and provide B cell help.

Within the context of this application, "T follicular regulatory cells" (or "Tfr") designates CD4+CXCR5+PD-1+ Bcl6+Foxp3+CD25− T lymphocytes.

Interleukin 2 (IL-2)

As used herein, Interleukin-2 (IL-2) encompasses mammal wild type Interleukin-2, and variants thereof. Preferably, IL-2 is a human IL-2, or a variant thereof.

Active variants of IL-2 have been disclosed in the literature. Variants of the native IL-2 can be fragments, analogues, and derivatives thereof. By "fragment" is intended a polypeptide comprising only a part of the polypeptide sequence. An "analogue" designates a polypeptide comprising the native polypeptide sequence with one or more amino acid substitutions, insertions, or deletions. Muteins and pseudopeptides are specific examples of analogues. "Derivatives" include any modified native IL-2 polypeptide or fragment or analogue thereof, such as glycosylated, phosphorylated, fused to another polypeptide or molecule, polymerized, etc., or through chemical or enzymatic modification or addition to improve the properties of IL-2 (e.g., stability, specificity, etc.). The IL-2 moiety of active variants (including fragments, analogues, and derivatives) generally has at least 75%, preferably at least 80%, 85%, more preferably at least 90% or at least 95% amino acid sequence identity to the amino acid sequence of the reference IL-2 polypeptide, for instance mature wild type human IL-2.

Methods for determining whether a variant IL-2 polypeptide is active are available in the art. An active variant is defined as a variant that shows an ability to stimulate Tregs, including variants with an improved ability, or a similar ability, or even a reduced ability to stimulate Tregs when compared to wild-type IL-2 or aldesleukin (as defined below), to the extent it does not stimulate Teffs more than it stimulates Tregs at the dosage herein defined. Methods for testing whether a candidate molecule stimulate T cells, and Tregs in particular, are well-known. Variants may be tested for their ability to stimulate effector T cells (such as CD8+ T cells and NK cells) or CD4+Foxp3+ Tregs.

A typical in vitro method for determining the ability of a candidate variant to preferentially stimulate Treg cells is described hereafter. Total PBMC are activated (e.g. at $4 \times 10^6$ cells per well) with anti-CD3 antibody (e.g. at 100 ng/ml), and cultured. On day 3 of culture, cells are typically washed and rested in fresh media for 3 days. Cells are then washed and contacted with IL-2 variants (e.g. at either 10 nM or 100 pM). About three days later, cells are counted and analyzed by flow cytometry.

Said active variants induce signaling events that preferentially induce survival, proliferation, activation and/or function of Treg cells. In certain embodiments, the IL-2 variant retains the capacity to stimulate, in Treg cells, STAT5 phosphorylation and/or phosphorylation of one or more of signaling molecules downstream of the IL-2R, e.g., p38, ERK, SYK and LCK. In other embodiments, the IL-2 variant retains the capacity to stimulate, in Treg cells, transcription or protein expression of genes or proteins, such as FOXP3 or IL-10, that are important for Treg cell survival, proliferation, activation and/or function. In other embodiments, the IL-2 variant exhibits a reduced capacity to stimulate endocytosis of IL-2/IL-2R complexes on the surface of CD25+ T cells. In other embodiments, the IL-2 variant demonstrates inefficient, reduced, or absence of stimulation of PI3-kinase signaling, such as inefficient, reduced or absent phosphorylation of AKT and/or mTOR (mammalian target of rapamycin). In yet other embodiments, the IL-2 variant retains the ability of wild type IL-2 to stimulate STAT5 phosphorylation and/or phosphorylation of one or more of signaling molecules downstream of the IL-2R in Treg cells, yet demonstrates inefficient, reduced, or absent phosphorylation of STAT5, AKT and/or mTOR or other signaling molecules downstream of the IL-2R in FOXP3− CD4+ or CD8+ T cells or NK cells. In other embodiments, the IL-2 variant is inefficient or incapable of stimulating survival, growth, activation and/or function of FOXP3− CD4+ or CD8+ T cells or NK cells.

In all cases, these variants have the capacity to stimulate cell lines such as CTLL-2 or HT-2 which can be universally used to determined their biological activity.

As used herein, "wild type IL-2" means IL-2, whether native or recombinant, having the 133 normally occurring amino acid sequence of native human IL-2 (SEQ ID NO: 1, which is the IL-2 sequence less the signal peptide, consisting of an additional 20 N-terminal amino acids), whose amino acid sequence is described in Fujita, et. al., PNAS USA, 80,7437-7441 (1983).

As used herein, "IL-2 mutein" means a polypeptide in which specific substitutions to the human mature interleukin-2 protein have been made.

Examples of IL-2 variants are disclosed, for instance, in EP109748, EP136489, U.S. Pat. No. 4,752,585; EP200280, EP118617, WO99/60128, EP2288372, U.S. Pat. Nos. 9,616, 105, 9,580,486, WO2010/085495, WO2016/164937.

For instance, certain mutations may result in a reduced affinity for the signaling chains of the IL-2 receptor (IL-2RR/CD122 and/or IL-2Ry/CD132) and/or a reduced capacity to induce a signaling event from one or both subunits of the IL-2 receptor. Other mutations may confer higher affinity for CD25 (IL-2Rα).

Particular examples of useful variants include IL-2 muteins which show at least one amino acid substitution at position D20, N30, Y31, K35, V69, Q74, N88, V91, or Q126, numbered in accordance with wild type IL-2, meaning that the chosen amino acid is identified with reference to the position at which that amino acid normally occurs in the mature sequence of wild type IL-2 of SEQ ID NO:1.

Preferred IL-2 muteins comprise at least one substitution at position D20H, D20I, D20Y, N30S, Y31H, K35R, V69AP, Q74, N88R, N88D, N88G, N88I, V91K, or Q126L We prefer conservative modifications and substitutions at other positions of IL-2 (i. e., those that have a minimal effect on the secondary or tertiary structure of the mutein).

Such conservative substitutions include those described by Dayhoff in The Atlas of Protein Sequence and Structure 5 (1978), and by Argos in EMBO J., 8: 779-785 (1989).

For example, amino acids belonging to one of the following groups represent conservative changes: -ala, pro, gly, gin, asn, ser, thr; -cys, ser, tyr, thr; -val, ile, leu, met, ala, phe; -lys, arg, his; -phe, tyr, trp, his; and -asp, glu.

Variants with mutations which disrupt the binding to the a subunit of IL-2R are not preferred, as those mutants may have a reduced capacity to stimulate Tregs.

IL-2 can be produced by DNA recombinant technique. The host organism used to express a recombinant DNA encoding IL-2 may be prokaryotic (a bacterium such as *E. coli*) or eukaryotic (e.g., a yeast, fungus, plant or mammalian cell). Processes for producing IL-2 have been described e.g., in U.S. Pat. Nos. 4,656,132; 4,748,234; 4,530,787; or U.S. Pat. No. 4,748,234, incorporated therein by reference.

Alternatively, IL-2 can be produced by chemical peptide synthesis. For instance, IL-2 can be produced by the parallel synthesis of shorter peptides that are subsequently assembled to yield the complete sequence of IL-2 with the correct disulfide bridge. A synthesis of Interleukin-2 is illustrated for instance in Asahina et al., Angewandte Chemie International Edition, 2015, Vol. 54, Issue 28, 8226-8230, the disclosure of which being incorporated by reference herein. In some embodiment, IL-2 is a variant having at least 80%, preferably at least 90%, 95%, 98%, 99%, sequence identity with a mature wildtype human IL-2. The variant can be glycosylated or non-glycosylated.

IL-2 is commercially available, including for pharmaceutical uses, and it is authorized for use in human patients. Suitable commercial forms include, e.g.

Proleukin® (aldesleukin) is a recombinant unglycosylated des-alanyl-1, serine-125 human interleukin-2, produced in *E. coli*.

Roncoleukin® is a recombinant human IL-2 produced in yeast.

In a preferred embodiment, IL-2 is aldesleukin. Aldesleukin is the active ingredient of Proleukin@. Aldesleukin is an unglycosylated variant of mature human IL-2 comprising two amino acid modifications as compared to the sequence of mature human IL-2: the deletion of the first amino acid (alanine) and the substitution of cysteine at position 125 by serine. Biosimilars of aldesleukin, showing the same amino acid sequence, are included.

The amino acid sequence of aldesleukin is provided as SEQ ID NO:2.

IL-2 for use in the present invention is preferably in essentially pure form, e.g., at a purity of 95% or more, further preferably 96, 97, 98 or 99% pure.

The biological activity of IL-2 is typically determined in a standard cell proliferation assay using an IL-2 dependent cell line, such as CTLL-2 or HT-2.

For instance, the biological activity of IL-2 may be determined by a cell-based assay performed on HT-2 cell line (clone AE, ATCC® CRL-1841™) whose growth is dependent on IL-2. Cell growth in the presence of a range of test interleukin-2 product is compared with the growth recorded with IL-2 international standard (WHO 2nd International Standard for INTERLEUKIN 2 (Human, rDNA derived) NIBSC code: 86/500). Cell growth is measured after addition and transformation of [3-(4,5-dimethylthiazol-2-yl)-5-(3-carboxymethoxyphenyl)-2-(4-sulfophenyl)-2H-tetrazolium (inner salt, MTS) into formazan by active viable cells. Formazan concentration is then measured by spectrophotometry at 490 nm.

In a preferred embodiment, IL-2 as used in the present invention is des-alanyl-1, serine-125 human interleukin-2, preferably produced recombinantly. In a particular embodiment it is unglycosylated, preferably it is produced in *E. coli*.

In a particular embodiment the IL-2 comprises a fusion protein. Preferably the fusion protein may comprise an IL-2 moiety and a moiety selected from the group consisting of an immunoglobulin or an immunoglobulin fragment (such as a Fc region of an immunoglobulin), serum albumin (such as human serum albumin), transferrin, and Fn3, or variants thereof.

In a particular embodiment, the IL-2 comprises an IL-2 moiety conjugated to a water-soluble polymer, preferably a non-protein polymer, such as polyethylene glycol (PEG). A preferred conjugate is described in patent application WO2012/065086, wherein the conjugate comprises a water-soluble polymer such as PEG covalently attached via a releasable linkage to an amine group of an IL-2 moeity.

In a particular embodiment, the IL-2 may be mutated at position D109C (with the C residue being capable of binding a PEG moiety), as described e.g. in international patent application WO2016/0025385.

In another particular embodiment, the IL-2 is fused to an immunoglobulin, preferably an IgG, preferably a human IgG, or preferably to a Fc region of an immunoglobulin. On may also use a particular fusion construct, that comprises two IL-2 proteins fused to one immunoglobulin, is disclosed e.g. in WO2014/023752 and WO2015/118016.

In another embodiment, the IL-2 is fused at the N-terminal end of a Fc moiety, either directly or preferably through a peptide linker, e.g. an 8 to 12 amino acid linker, as described e.g. in international patent application WO2016/014428.

IL-1 Inhibitors

IL-1 may be naturally produced in two forms: IL-1 alpha and IL-1 beta. In the present invention, and unless otherwise specified, the term "IL-1" thus includes IL-1 alpha (also designated IL-1α or IL-1a) or IL-1 beta (also designated IL-1β or IL-1b).

A third cytokine in the system acts as an antagonist and is referred to as IL-1 receptor antagonist (IL-1ra).

There are three known IL-1 receptor subunits. The active receptor complex consists of the type I receptor (IL-1R1) and IL-1 receptor accessory protein (IL-1RAcP, also referred to as IL-1R3).

IL-1R1 is responsible for binding the three naturally occurring ligands (IL-1 alpha, IL-1 beta and IL-1ra) and is able to do so in the absence of the IL-1RAcP. However, signal transduction requires interaction of IL-1R1 bound to IL-1 with IL-1RAcP. IL-Ira bound to IL-1R1 does not allow an interaction with the IL-1RAcP and hence cannot signal. A third receptor subunit, the type 2 receptor (IL-1 R2), binds IL-1 alpha or IL-1 beta but cannot signal because it lacks an intracellular domain. Instead, it inhibits IL-1 bioactivity by acting as a decoy receptor in both a membrane-bound form and a cleaved, secreted form. IL-1ra inhibits IL-1 alpha and IL-1 beta by binding to IL-1 R1 but not transducing an intracellular signal or a biological response. IL-1ra inhibits the biological activities of IL-1 both in vitro and in vivo. A recombinant form of IL-1ra produced in *E. coli* is currently approved for pharmaceutical use in the United States and Europe. This drug has the generic name anakinra and is marketed under the trade name Kineret®.

"IL-1 inhibitors" as used throughout this specification refer to molecules that decrease the bioactivity of IL-1 alpha, IL-1 beta, or IL-1 receptor type 1 (IL-1 R1), whether by direct or indirect interaction with IL-1 alpha, IL-1 beta, IL-1 R1, IL-1 receptor accessory protein (IL-1 RacP), interleukin-1 converting enzyme (ICE), with proteins that mediate signaling through a receptor for IL-1 alpha or beta, with proteins controlling the expression or release of IL-1a, IL-1 beta, IL-1 R1 or IL-1 R2. Inhibition of IL-1 may result from a number of mechanisms, including down-regulation of IL-1 transcription, expression, functional maturation, or release from cells that produce IL-1; binding of free IL-1; interference with binding of IL-1 to its receptor; interference with formation of the IL-1 receptor complex (i.e., association of the IL-1 receptor type I with IL-1 RacP); and interference with modulation of IL-1 signaling after binding to its receptor. Thus, the term "IL-1 inhibitor" includes, but is not limited to, IL-1 beta inhibitors and IL-1 receptor antagonists (IL-1ra), such as anakinra and antibodies to IL-1 R1. Biosimilars of anakinra, showing the same amino acid sequence, are included.

Inhibition of IL-1 signalling at the receptor level is illustrated in Boraschi et al. Immunological Reviews. 2018; 281:197-232.

Classes of IL-1 inhibitors include the following, which are described in detail further hereinbelow: Interleukin-1 receptor antagonists such as IL-1ra and anti-IL-1 receptor monoclonal antibodies, as described below; IL-1 binding proteins such as soluble IL-1 receptors, anti-IL-1 monoclonal antibodies; inhibitors of interleukin-1 beta converting enzyme (ICE) or caspase I (e.g., WO 99/46248, WO 99/47545, and WO 99/47154), which can be used to inhibit IL-1 beta production and secretion; interleukin-1 beta protease inhibitors; and compounds and proteins that block in vivo synthesis or extracellular release of IL-1.

The term "IL-1 binding proteins" refers to molecules that bind to IL-1 and thus prevent IL-1 beta from exerting bioactivity when bound to IL-1 R1. Thus, IL-1 beta inhibitors include, but are not limited to, IL-1 beta antibodies, peptides that bind to IL-1 beta, peptibodies that bind to IL-1 beta, soluble IL-1 receptor molecules, and IL-1 trap molecules.

The term "IL-1 receptor antagonists" refers to molecules that bind to IL1 R1 or IL-1RacP or otherwise prevent the interaction of IL-1 R1 and IL-1RacP. Thus, the term "IL-1 receptor antagonists" includes, but is not limited to anakinra, Fc-IL-1ra, IL-IR1 antibodies, IL-1RacP antibodies, peptides that bind to IL-1 R1 or to IL-1RAcP, and peptibodies that bind to IL-1R1 or IL-1RAcP.

Exemplary IL-1 inhibitors are disclosed in the following references:

U.S. Pat. Nos. 5,747,444; 5,359,032; 5,608,035; 5,843,905; 5,359,032; 5,866,576; 5,869,660; 5,869,315; 5,872,095; 5,955,480; 5,965,564;

International (WO) patent applications 98/21957, 96/09323, 91/17184, 96/40907, 98/32733, 98/42325, 98/44940, 98/47892, 98/56377, 99/03837, 99/06426, 99/06042, 91/17249, 98/32733, 98/17661, 97/08174, 95/34326, 99/36426, 99/36415;

European (EP) patent applications 534978 and 894795; and French patent application FR 2762514.

For purposes of the present invention, IL-1ra and variants and derivatives thereof as discussed hereinafter are collectively termed "IL-1ra protein(s)". The molecules described in the above references and the variants and derivatives thereof discussed hereinafter are collectively termed "IL-1 inhibitors". IL-1ra is a human protein that acts as a natural inhibitor of interleukin-1 and which is a member of the IL-1 family member that includes IL-1a and IL-1 beta. Preferred receptor antagonists (including IL-1ra and variants and derivatives thereof), as well as methods of making and using thereof, are described in WO 91/08285; WO 91/17184; AU 9173636; WO 92/16221; WO93/21946; WO 94/06457; WO 94/21275; FR 2706772; WO 94/21235; DE 4219626, WO 94/20517; WO 96/22793; WO 97/28828; WO 99/36541, and U.S. Pat. Nos. 5,075,222 and 6,599,873. The proteins include glycosylated as well as non-glycosylated IL-1 receptor antagonists.

Those skilled in the art understand that many combinations of deletions, insertions and substitutions (individually or collectively "variant(s)") can be made within the amino acid sequences of IL-1ra, provided that the resulting molecule is biologically active (e.g., possesses the ability to inhibit IL-1).

Particular variants are described in U.S. Pat. No. 5,075,222.

Anakinra is a recombinant, nonglycosylated form of the human interleukin-1 receptor antagonist (IL-1Ra), differing from native human IL-1Ra in that it has the addition of a single methionine residue at its amino terminus.

The term "IL-1 receptor antagonist" further includes modified IL-1ra and fusion proteins comprising IL-1ra. Exemplary fusion proteins include Fc-IL-1ra, and molecules as described in U.S. Pat. No. 6,294,170.

"IL-1 beta antibodies, "anti-IL-1 beta antibodies" and "antibodies to IL-1 beta" refer to antibodies that specifically bind to IL-1 beta.

Several antibodies to IL-1 beta have previously been reported. R&D Systems, Inc. produces and sells the murine anti-human IL-1 beta/IL-1F2 antibody MAB201 (R&D Systems, Inc., cat. no. MAB201), a full-length immunoglobulin IgG1, which is produced in hybridoma culture.

MAB201 has been humanized by grafting its CDRs onto human kappa chain germline sequence and gamma chain VH-2 acceptor sequences (US20030026806). XOMA052, also known as AB7 or gevokizumab, is a humanized IgG2, i.e. a full-length immunoglobulin (EP 1899378 B). Its variable domains were humanized to match a human kappa 1 light chain and a human VH2 heavy chain. Its CDRs are identical to MAB201 with the exception of one conservative point mutation in CDR-H2.

In a particular embodiment, the IL-1 inhibitor is ACZ885 (canakinumab) which is a selective, high-affinity, fully human monoclonal antibody that inhibits IL-1 beta. Biosimilars of canakinumab, which show the same amino acid sequence, are also encompassed.

Additional IL-1 beta antibodies may be produced as described hereinafter. Further examples of anti IL-1 antibodies are described in WO 9501997, WO 9402627, WO 9006371, EP 364778, EP 267611, EP 220063, and U.S. Pat. No. 4,935,343.

Antibodies having specific binding affinity for IL-1 beta can be produced through standard methods. Alternatively, antibodies may be commercially available. The terms "antibody" and "antibodies" include polyclonal antibodies, monoclonal antibodies, humanized or chimeric antibodies, single chain Fv antibody fragments, Fab fragments, and F(ab)2 fragments.

Likewise, "IL-1 R1 antibodies", "anti-IL1R1 antibodies" and "antibodies to IL-1 R1" refer to antibodies that specifically bind to IL-1 R1. Examples of IL-1 R1 antibodies are described in EP 623 674 and U.S. Pat. App. 2004/0097712, published May 20, 2004 (U.S. Ser. No. 10/656,769). Additional IL-1 R1 antibodies may be produced as described hereinafter.

The terms "antibody" and "antibodies" as used herein refer to intact antibody, or a binding fragment thereof that competes with the intact antibody for specific binding and includes chimeric, humanized, fully human, and bispecific antibodies. In certain embodiments, binding fragments are produced by recombinant DNA techniques. In additional embodiments, binding fragments are produced by enzymatic or chemical cleavage of intact antibodies. Binding fragments include, but are not limited to, Fab, Fab', F(ab')2, Fv, and single-chain antibodies. Monoclonal antibodies, which are homogeneous populations of antibodies to a particular epitope contained within an antigen, can be prepared using standard hybridoma technology. In particular, monoclonal antibodies can be obtained by any technique that provides for the production of antibody molecules by continuous cell lines in culture such as described by Kohler, G. et al., Nature, 1975, 256:495, the human B-cell hybridoma technique (Kosbor et al., Immunology Today, 1983, 4:72; Cole et al, Proc. Natl. Acad. Sci USA, 1983, 80:2026), and the EBV-hybridoma technique (Cole et al., Monoclonal Antibodies and Cancer Therapy, Alan R. Liss, Inc., 1983, pp. 77-96). Such antibodies can be of any immunoglobulin class including IgG, IgM, IgE, IgA, IgD, and any subclass thereof. The hybridoma producing the monoclonal antibodies of the invention can be cultivated in vitro or in vivo.

Antibody fragments that have specific binding affinity for IL-1 beta can be generated by known techniques. For example, such fragments include, but are not limited to, F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., 1989, Science, 246: 1275. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques. See, for example, U.S. Pat. No. 4,946,778.

A "Fab fragment" is comprised of one light chain and the CHI and variable regions of one heavy chain. The heavy chain of a Fab molecule cannot form a disulfide bond with another heavy chain molecule.

A "Fab' fragment" contains one light chain and one heavy chain that contains more of the constant region, between the CHI and CR2 domains, such that an interchain disulfide bond can be formed between two heavy chains to form a F(ab')2 molecule. A "F(ab')2 fragment" contains two light chains and two heavy chains containing a portion of the constant region between the CHI and CH2 domains, such that an interchain disulfide bond is formed between two heavy chains.

The "Fv region" comprises the variable regions from both the heavy and light chains, but lacks the constant regions. "Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203.

The term "soluble IL-1 receptor molecules" refers to soluble IL-1R1 (sIL-1R1), soluble IL-1R2 (sIL-1 R2), and soluble IL-1RacP (sIL-1RacP); fragments of sIL-1 R1, sIL-1 R2, and sIL-1RacP; and fusion proteins of sIL-1R1, sIL-1R2, sIL-1RacP and fragments of any thereof, including "IL-1 trap" molecules and fusion proteins with human serum albumin, transthyretin or an Fc domain; and derivatives of any of the foregoing (e.g., soluble receptor linked to polyethylene glycol).

Soluble IL-1 receptor molecules are described in U.S. Pat. Nos. 5,492,888; 5,488,032; 5,464,937; 5,319,071; and 5,180,812. Fragments of the IL-1 receptor include, but are not limited to, synthetic polypeptides corresponding to residues 86-93 of the human type 1 IL-1 receptor, which bind IL-1alpha and beta and inhibit IL-1 activity in vitro and in vivo. See Tanihara et al. (1992) Biochem. Biophys. Res. Commun. 188: 912.

Rilonacept, a product of TRAP (Target-Related Affinity Profiling) technology developed by Regeneron pharmaceuticals, is a dimeric fusion protein composed of the ligand binding domains of the extracellular portions of the human IL-IR1 and the IL-1RAcP linked to the human IgG1 Fc domain. Rilonacept, (also known as IL-1trap) is described in U.S. Pat. No. 5,844,099. Rilonacept acts similar to the endogenous IL-IRA soluble decoy receptor by binding IL-1β but with 100 times greater affinity than native receptors. The drug is also able to bind IL-1RA and IL-1α though with lower affinity. Rilonacept acts to sequester IL-1 and thereby prevents interaction with endogenous cell-surface receptors, resulting in a reduction of IL-1-mediated signal transduction events. Biosimilars of rilonacept, which show the same amino acid sequence, are included in the present invention.

Conjugates

In a particular embodiment, it is provided a conjugate comprising IL-2 conjugated to an IL-1 inhibitor.

The term "conjugate" means that the IL-2 entity and the IL-1 inhibitor entity are covalently linked.

The conjugation may be a direct protein fusion, or a peptide linker may be used to link the two entities. Such peptide linkers are described, e.g. in Chen et al, Adv Drug Deliv Rev. 2013; 65(10): 1357-1369. One may use flexible linkers, rigid linkers, or in vivo cleavable linkers.

Typically a peptide linker may be a peptide of 2 to 15 amino acids, preferably 2 to 10 amino acids.

The flexible linkers are often rich in small or hydrophilic amino acids such as Gly or Ser to provide the structural flexibility and have been applied to connect functional domains that favor interdomain interactions or movements. In cases where sufficient separation of protein domains is required, rigid linkers may be preferable. By adopting α-helical structures or incorporating Pro, the rigid linkers can efficiently keep protein moieties at a distance. Both flexible and rigid linkers are stable in vivo, and do not allow the separation of joined proteins. Cleavable linkers, on the other hand, permit the release of free functional domain in vivo via reduction or proteolytic cleavage. The rational choice of linkers should be based on the properties of the linkers and the desired fusion proteins.

Alternatively, the IL-2 and the IL-1 inhibitor may be crosslinked, i.e. conjugated by a non-peptide, chemical, covalent bond. For that purpose, crosslinking reagents may be used, that contain reactive ends to specific functional groups, such as primary amines and sulfhydryls, on the IL-2 entity and the IL-1 inhibitor entity. Homobifunctional, amine-reactive NHS esters or imidates, and heterobifunctional, amine-reactive, photoactivatable phenyl azides are the most commonly used crosslinkers, as described in greater details below.

Homobifunctional amine-specific protein crosslinking reagents are based on NHS-ester and imidoester reactive groups for selective conjugation of primary amines.

Crosslinking reagents based on maleimide and hydrazide reactive groups may also be contemplated for conjugation and formation of covalent crosslinks The conjugates may alternatively be produced using homobifunctional sulfhydryl-specific crosslinking reagents based on maleimide or pyridyldithiol reactive groups for selective covalent conjugation of protein and peptide thiols (reduced cysteines) to form stable thioether bonds.

Another possibility is to use aryl azide, diazirine, and other photo-reactive (light-activated) chemical heterobifunctional crosslinking reagents.

Heterobifunctional protein crosslinking reagents for conjugation between primary amine (lysine) and sulfhydryl (cysteine) groups of proteins may have a variety of lengths.

Carbodiimide crosslinking reagents, DCC and EDC (EDAC), are typically used for conjugating carboxyl groups (glutamate, aspartate, C-termini) to primary amines (lysine, N-termini) and also N-hydroxysuccinimide (NHS) for stable activation of carboxylates for amine-conjugation.

Dosage and Regimen

In a particular embodiment, IL-2 and the IL-1 inhibitor are separate entities and are comprised in the same pharmaceutical composition.

Alternatively, they can be administered separately, either simultaneously or sequentially.

The standard measure of an amount IL-2 is the International Unit (IU), which technically is not a fixed weight but the amount that produces a fixed biological effect in a specific cell proliferation assay, as determined by the World Health Organization (WHO). The reason is that i) the weight varies depending on the exact sequence of the molecule and its glycosylation profile, and ii) what matters is the activity, not the weight of the molecule.

The principle of the International Unit is precisely to provide a standard to which any IL-2 molecule can be compared (regardless of their source, or their sequence, including wild-type or active variant sequences).

In practice, the WHO provide ampoules containing an IL-2 molecule that has been calibrated and serves as the reference to determine the dosage of a given preparation of IL-2 (again regardless of the source or sequence of said IL-2) defined by its potency. For instance, to determine the dosage of a given preparation of IL-2, the biological activity of the candidate IL-2 preparation is measured in a standard cell proliferation assay using an IL-2 dependent cell line, such as CTLL-2, and compared with the biological activity of the standard. The cells are grown in the presence of different doses of the standard. A dose-response effect of IL-2 is established, where the dose of IL-2 is plotted on the X axis as IU and the measure of proliferation (pr) is on the Y axis. When one wants to determine the activity of any IL-2 product of unknown activity, the product is used to grow the Il-2 dependent cells and the proliferation is measured. The pr value is then plotted on the Y axis and from that value a line parallel to the X axis is drawn. From the point of intersection of this line with the dose response line, a line parallel to the Y axis is then drawn. Its intersection with the X axis provides the activity of the candidate IL-2 product in IU.

Any change of the WHO standard ampoules does not impact the International Unit nor the determination of a dosage of any IL-2 preparation.

The 1st standard (WHO international Standard coded 86/504, dated 1987) contained a purified glycosylated IL-2 derived from Jurkat cells and was arbitrarily assigned a potency of 100 IU/ampoule. As the stocks of the 1st international standard (IS) were running low, the WHO had to replace it. The WHO provided another calibrated IL-2 ampoule, this time produced using *E. coli*. The 2nd standard ampoules contained 210 IU of biological activity per ampoule. The change of standard ampoules does not mean that the IU changes. So, determining the dosage of a test IL-2 preparation will not vary whether one uses the 1st standard ampoule or the 2nd standard ampoule, or a subsequent standard ampoule, as a reference.

According to the invention, IL-2 is preferably administered at a dosage ranging from about 0.5 to 3.5 MIU/day, preferably between about 1 MIU/day to about 2 MIU/day. This dosage is particularly suitable for human subjects.

This dosage effectively activates Tregs without substantially activating Teffs. The consequence is a dramatic increase in the Treg/Teff balance in the subject. At this dosage IL-2 substantially avoids side effects, while very substantially inducing Tregs.

In a preferred embodiment, particularly advantageous for subcutaneous administration, IL-2 is administered at a dose of 1, 1.5 or 2 MIU/day.

According to the invention, the treatment typically comprises at least a first course wherein interleukin-2 is administered once per day during at least about 2 or 3 consecutive days, preferably during 3 to 7, still preferably during 4 to 5 consecutive days, preferably followed by a maintenance dose after about six days or about 1 to about 4 weeks.

The maintenance dose is typically administered during at least one month, preferably at least about 3 months, still preferably at least about 6 months. In a preferred embodiment, the maintenance dose is administered between about 3 months and about 12 months, preferably between about 6 months and about 12 months.

In a preferred embodiment, the maintenance treatment consists of an administration of interleukin-2 once or twice a week, or every one or two weeks.

In another embodiment, the IL-2 is given every other day for 1 to 2 weeks, in cycles that can be repeated after break of administration that can last from 3 days to 3 months, preferably from one to 4 weeks.

In a preferred embodiment, the maintenance treatment consists of an administration of interleukin-2 once or twice a week, every one or two weeks, during a period of at least one month, preferably from about 3 months to about 12 months.

Preferably the maintenance dosage is substantially the same as the first course dosage, or it can be a lower or higher dosage.

In a preferred embodiment, the treatment comprises at least a first course wherein interleukin-2 is administered at a dosage of at most 3.5 MIU/day, preferably about 1 to about 2MIU/day, preferably 1-1.5 MIU/day, once per day during 2 or 3 to 7 days, preferably 5 days, followed by a maintenance dose after one to two weeks, of about 1 to about 2MIU/day, preferably 1-1.5 MIU/day every 2 weeks, during at least three months, preferably at least six months.

In another embodiment, especially when the IL-2 molecule is a variant with longer half-life and/or is conjugated to a moiety that improves the half-life of the conjugate, the regimen is adjusted to the extent the Treg increase during maintenance remains at least 1.3, 1.5, 1.7, 1.9, or at least twice the baseline Treg level. For that purpose, in an embodiment, the regimen may be defined as a first (induction) course consisting of a dosage of at most 3.5MIU one per day during 1 to 3 days, followed by a maintenance course after 1 to 4 weeks. Preferably the maintenance course then consists in an administration of IL-2 at a maintenance dosage, once every 2 weeks to once a month, during about 1 month, preferably 3 months, still preferably 6 months, or more.

According to the present invention, the subject it administered with IL-2, as well as with an IL-1 inhibitor, either simultaneously or sequentially.

Additional active ingredients may be administrated, either in combination or separately, such as methotrexate, a corticosteroid, and/or nonsteroidal anti-inflammatory drugs (NSAIDs). However, in preferred embodiments, the dosage of such additional active ingredients can be reduced dramatically, reducing the risk and severity of side effects.

A typical daily dosage for the IL-1 inhibitor may range from about 0.1 mg/kg to up to 100 mg/kg or more, depending on the route of administration, and the condition of the patient. For instance, anakinra may be used at a dosage of 20 to 200 mg/day, preferably 50 to 100 mg/day.

In certain embodiments, the composition or compositions may be administered as a single dose, or as two or more doses of one or more of the therapeutic molecules (namely IL-2 and the IL-1 inhibitor). These doses can consist of the same or different amounts of the therapeutic molecules and can be administered at the same or different times via the same or different routes of administration. In certain embodiments, the composition may be administered as a composition comprising any one or any combination of the therapeutic molecules. In certain embodiments, the combination may include the same or different amounts of the therapeutic molecules.

Administration Forms and Routes

The therapeutic molecules (IL-2 and/or the IL-1 inhibitor) may be administered using any convenient route, including parenteral, e.g. intradermal, subcutaneous, or intranasal route. The subcutaneous route is preferred. Oral, sublingual or buccal administrations are also encompassed.

The therapeutic molecules (IL-2 and/or the IL-1 inhibitor) may be administered by distinct routes, or, preferably, by the same administration route.

The therapeutic molecules (IL-2 and/or the IL-1 inhibitor) are typically administered in association (e.g., in solution, suspension, or admixture) with a pharmaceutically acceptable vehicle, carrier or excipient. Suitable excipients include any isotonic solution, saline solution, buffered solution, slow release formulation, etc. Liquid, lyophilized, or spray-dried compositions comprising IL-2 or variants thereof are known in the art and may be prepared as aqueous or nonaqueous solutions or suspensions. Preferably the pharmaceutical compositions comprise appropriate stabilizing agents, buffering agents, bulking agents, or combinations.

An example of an IL-2 formulation suitable for a subcutaneous injection is described in international patent application WO2017/068031.

Auto-Immune and/or Inflammatory Disorders

The combination of IL-2 and the IL-1 inhibitor is useful in treating auto-immune and/or inflammatory disorder, such as systemic lupus erythematosus, type I diabetes, HCV-related vasculitis, uveitis, myositis, systemic vasculitis, psoriasis, allergy, asthma, Crohn's disease, multiple sclerosis, rheumatoid arthritis, atherosclerosis, autoimmune thyroid disease, auto-inflammatory diseases, neuro-degenerative diseases, Alzheimer's disease, graft-versus-host disease, spontaneous abortion and allograft rejection; solid organ transplantation rejection, vasculitis, inflammatory bowel disease (IBD), and allergic asthma; spondyloarthritis or ankylosing Spondylitis; Sjogren's syndrome, Systemic sclerosis, Alopecia aerate, or Ulcerative Colitis.

In a preferred embodiment, a combination of IL-2 and anakinra is used for treating a subject affected with systemic lupus erythematosus (SLE).

In a particular embodiment, patients have active SLE despite stable background therapy, including oral corticotherapy. In particular embodiments, patients with active SLE may be characterized by:

SELENA-SLEDAI score ≥6

Positive for Anti-nuclear antibody (ANA), (e.g. titer ≥1:80)

Positive for anti-dsDNA antibody

Low levels (below the laboratory normal range) of C3 or C4 complement fractions OR a SELENA-SLEDAI score ≥8

In preferred protocols, the treatment comprises at least a first course wherein interleukin-2 is administered once per day during at least 3 consecutive days, followed by a maintenance treatment after 1 to 4 weeks; while the IL-1 inhibitor is administered daily for about two months.

A preferred protocol may consist of:

IL-2 (such as aldesleukin) at 1.5 MIU/day by subcutaneous injection, given first every day for 5 days, then every week from day 15 up to week 48.

An IL-1 inhibitor such as anakinra at 100 mg/day by subcutaneous injection, given every day for 8 weeks.

Such treatment is particularly useful in treating patients with SLE, such as those described above.

Depending on the formulation, both active ingredients can be injected at separate sites, or as a unique pharmaceutical composition administered subcutaneously at a single site.

This combination treatment should improve the response rate, for example assessed by the decrease of ANA and anti-dsDNA antibodies.

The below examples illustrate the invention without limiting its scope.

EXAMPLES

Example 1: Mice Model of Colitis

Dextran Sulfate Sodium (DSS) is added to drinking water from day 0 to day 5. Mice are monitored three times a week for body weight, stool consistency and presence of blood in the stool (Disease Activity Index assessment).

Mice were daily injected intraperitoneally with 50000 international units of aldesleukin or with 10 μg/mouse/day of anakinra, or both, during five consecutive days corresponding to the period of DSS water exposure.

Figure 1:
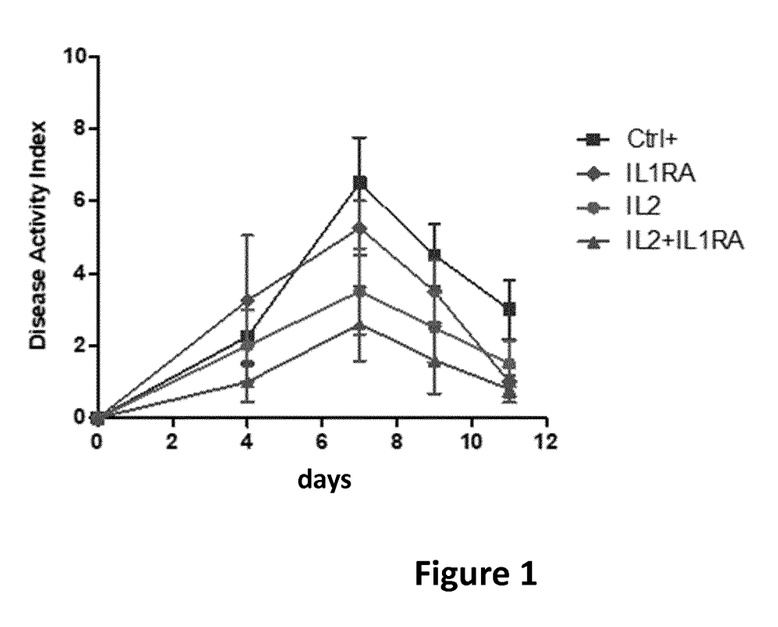
FIG. 1 represents a graph showing the evolution of the Disease Activity Index in mice with Dextran Sulfate Sodium (DSS) induced colitis treated with anakinra ("IL1Ra"), aldesleukin ("IL2") or both. CTRL+=control.

FIG. 1 shows that the Disease Activity Index is reduced in the mice that were injected with aldesleukin and even more in the mice that were administered with the combination of aldesleukin and anakinra, compared to the ones which received anakinra only and to the controls.

Example 2: Mice Model of Multiple Sclerosis

Mice. Six weeks old C57BL/6 (Jrj) female mice were purchased from Janvier Labs.

EAE model and treatment. 200 μL of 100 μg myelin oligodendrocyte glycoprotein (MOG$_{35-55}$) peptide (Tocris Biosciences) emulsified in complete Freund's adjuvant (Sigma Aldrich) containing 5 mg/mL killed *Mycobacterum tuberculosis* (strain H37Ra, BD Biosciences) was injected subcutaneously on Day 0. Following immunization, 200 ng of pertussis toxin (Enzo Life Sciences) was injected i.v. into mice on Day 0 and Day 2. Aldesleukin and/or anakinra (Kineret®, Sobi) was administered during 5 days before the immunization (Day −5 to Day −1). Mice were injected with either 25.000 IU/day of aldesleukin or 10 μg of anakinra or both or PBS during 5 days by daily i.p. injections.

Clinical scores (0—no symptoms; 0.5—partial limp tail; 1—limp tail; 1.5—impaired righting reflex; 2—absence of righting reflex; 2.5—partial paralysis of hind limbs; 3—total paralysis of hind limbs; 3.5—partial paralysis of front limb; 4—total paralysis of front limb; 5—death) were recorded every 2 or 3 days.

Statistics. Clinical scores for each treated group (n=6 mice) were evaluated using a 2-way RM ANOVA test versus the control group (PBS). A p value ≤0.05 was considered statistically significant. Mean+/−standard errors of the means (SEM) are represented for each group. All statistical analysis were performed using Prism v6 (GraphPad Software).

Figure 2:
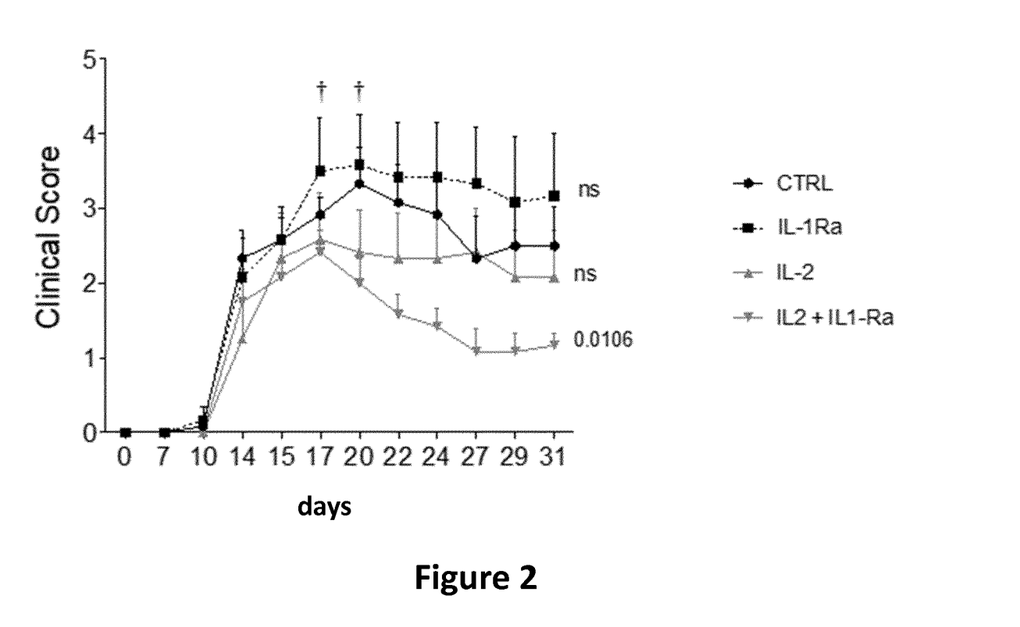
FIG. 2 represents a graph showing the evolution of the Clinical Score in Experimental autoimmune encephalomyelitis (EAE) mice models treated with anakinra ("IL1Ra"), aldesleukin ("IL2") or both. CTRL=control.

FIG. 2 shows that the Clinical Score is reduced in the mice that received aldesleukin injections and even more in the ones which received the combination of aldesleukin and anakinra, compared to the ones that received anakinra only and to the controls. The effect is synergistic.

Example 3: Mice Model of Pristane-Induced Systemic Lupus Erythematosus (SLE), Preventive Treatment Mice. Eight weeks old C57BL/6 (Jrj) female mice were purchased from Janvier Labs.

Pristane-induced SLE and treatment. 500 μl of Pristane (Sigma-Aldrich) was injected intraperitoneally at Day 0.

Id-IL2: Low-dose of aldesleukin was injected at dose of 50000 IU/day during 5 days before the immunization (Day −5 to Day −1). IL1Rn Adeno-Associated Virus (AAV) coding for IL1Ra were administered intraperiteonally at D-10 before pristane administration to ensure IL1Ra production at the beginning of the experiment. A combination of the treatment was evaluated by both reagent injections in the same protocol. Clinical manifestation of SLE was evaluated by detection of anti-dsDNA and anti-smRNP IgG autoantibodies in sera. Moreover, total proteinuria was assessed to evaluate kidney damages.

Figure 3:
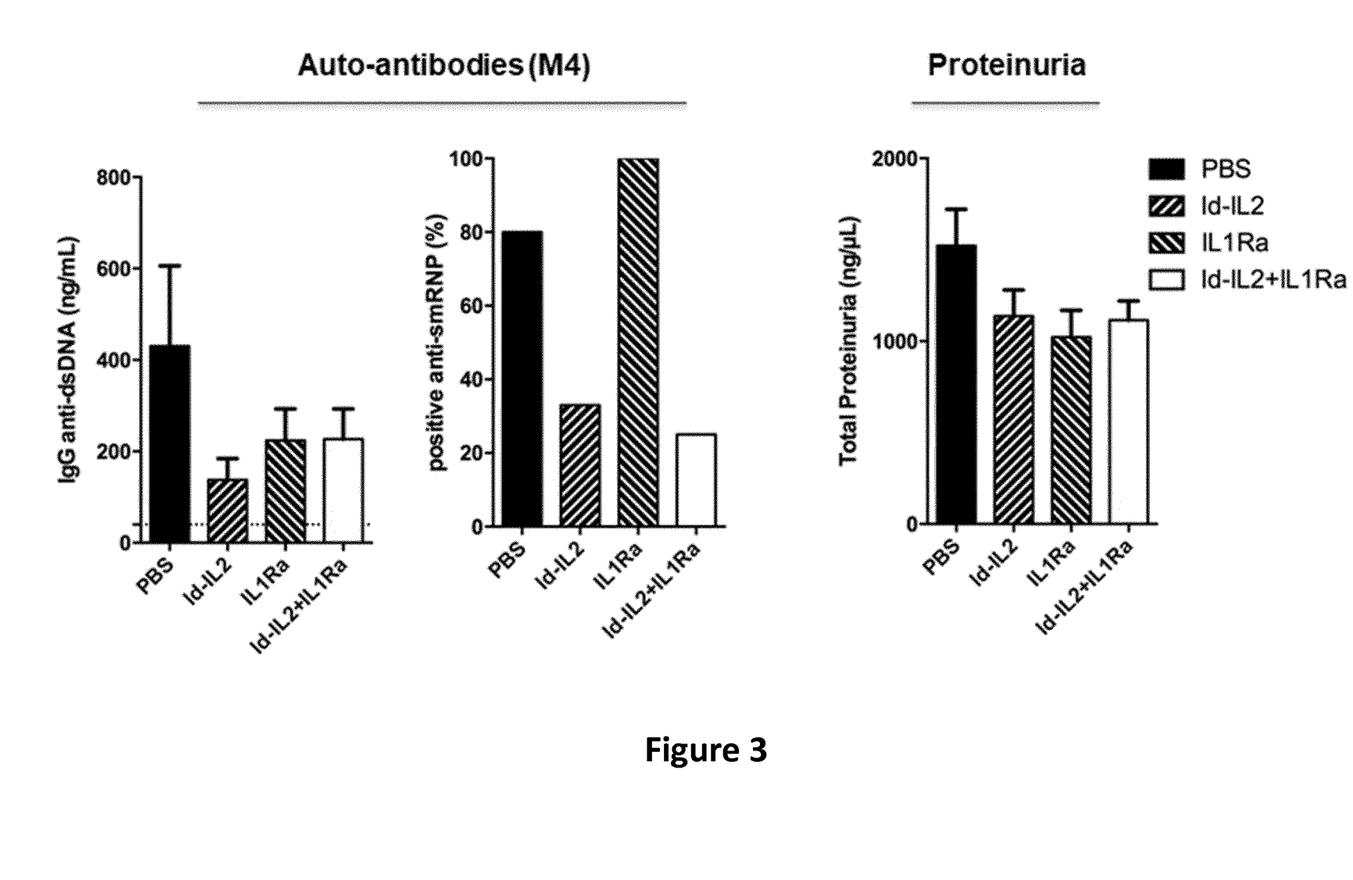
FIG. 3 represents graphs showing anti-dsDNA autoantibodies and proteinuria in mice model of Pristane-induced Systemic Lupus Erythematosus (SLE), under a preventive treatment with ("IL1Ra"), aldesleukin ("IL2") or both. PBS (phosphate buffer saline) serves as control.

FIG. 3 shows that 4 months after disease initiation, Id-IL2 can control anti-dsDNA antibodies apparition as well as Il1Ra and the combination. However, IL1Ra alone failed to control development of anti-smRNP antibodies while Id-IL2 and even more the combination of both controlled this development in almost 80% of treated mice. This control of autoantibodies development is related to a control of the increase of total proteinuria at the same timepoint showing the importance of controlling autoantibodies development to avoid kidney damages.

Example 4: Mice Model of Pristane-Induced Systemic Lupus Erythematosus (SLE). Curative Treatment Mice. Eight weeks old Balb/c (Jrj) female mice were purchased from Janvier Labs.

Pristane-induced SLE and treatment. 500 μl of Pristane (Sigma-Aldrich) was injected intraperitoneally at Day 0. Treatment period occurred during 1 month starting at Month 1 (M1).

Id-IL2: 50000 IU of aldesleukin was injected intraperitoneally (i.p.) 5 days a week during the treatment period. Anakinra was administered i.p. at a dose of 50 mg/kg, 5 days a week during the treatment period. In order to assess the combination of both treatments, both injections were administered in parallel. Clinical manifestation of SLE was evaluated by detection of anti-dsDNA and anti-smRNP IgG autoantibodies in sera. Moreover, total proteinuria was assessed to evaluate kidney damages.

Figure 4:
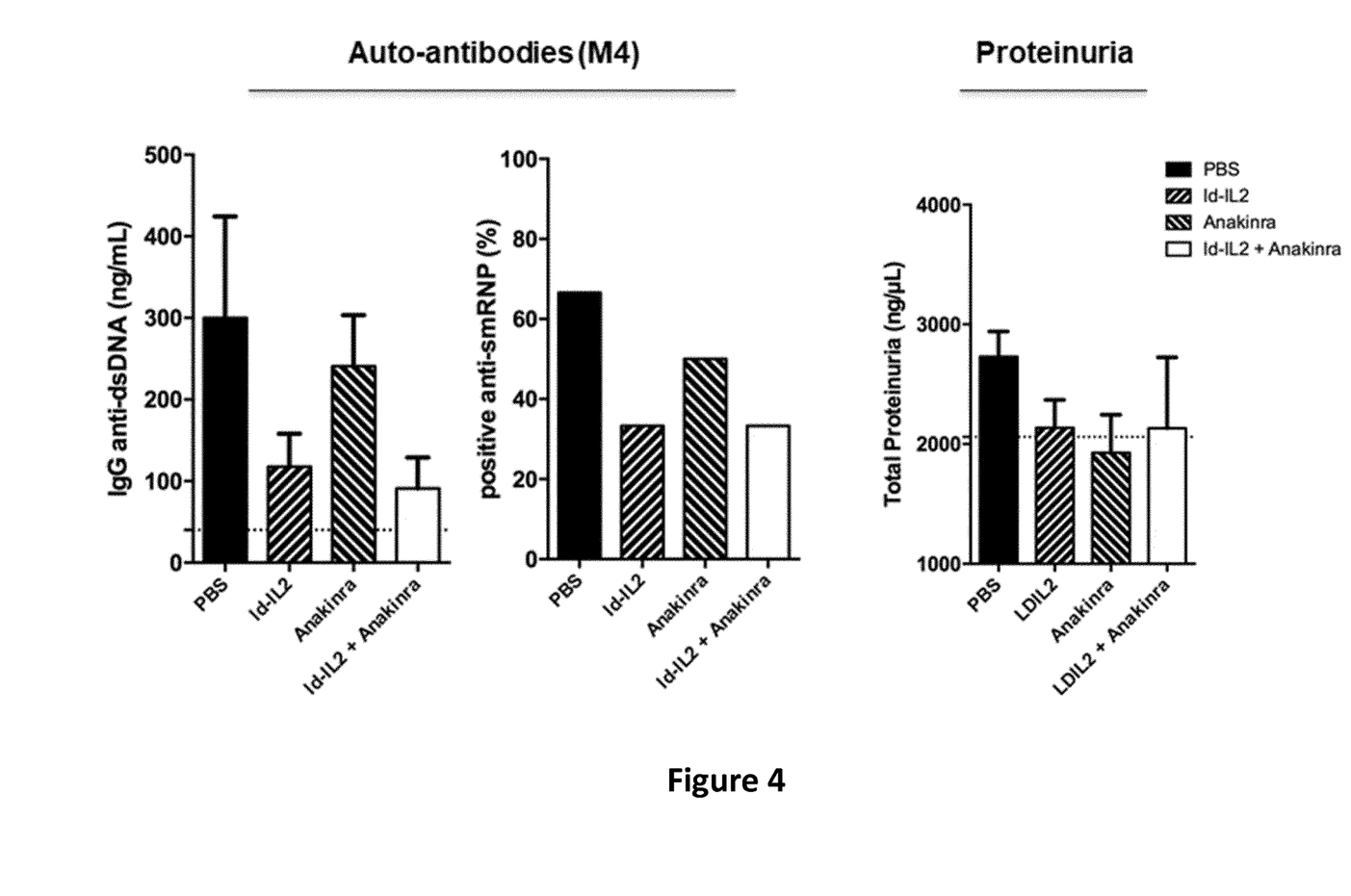
FIG. 4 represents graphs showing anti-dsDNA autoantibodies and proteinuria in mice model of Pristane-induced Systemic Lupus Erythematosus (SLE), under a curative treatment with ("IL1Ra"), aldesleukin ("IL2") or both. PBS (phosphate buffer saline) serves as control.

FIG. 4 shows that 4 months after disease initiation, curative treatment showed similar results than preventive results, where addition of Id-IL2 to anakinra treatment increased control of autoantibodies development. Moreover, all treatment regimens showed a slight decrease in total proteinuria relating the control of kidney damages to autoantibodies development prevention.

Figure 5:
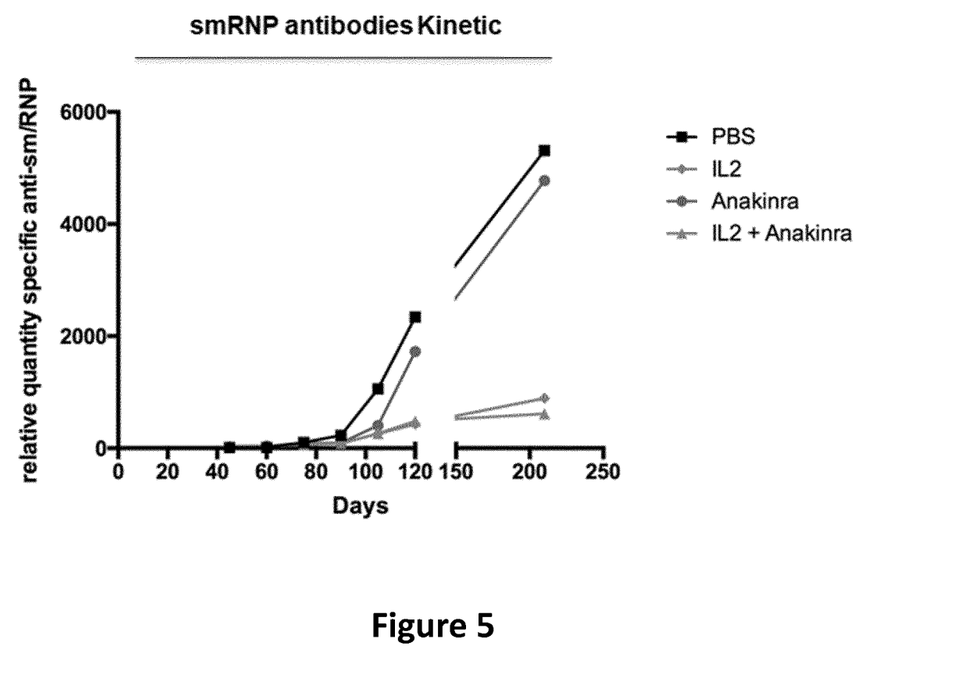
FIG. 5 shows the evolution of SLE-specific anti-smRNP autoantibodies in the pristane-induced SLE, under a curative treatment with ("IL1Ra"), aldesleukin ("IL2") or both.

FIG. 5 shows that long-term follow-up of SLE-specific anti-smRNP autoantibodies was controlled by the curative treatment with Id-IL2 whereas anakinra alone completely failed to control their production. Moreover, combination of both treatments showed a complete long-term control of anti-smRNP autoantibodies, even better than Id-IL2 alone, 7 months after disease initiation.

The invention claimed is:

1. A method for increasing regulatory T cells and reducing inflammation in a subject in need thereof, the method comprising administering to the subject a combination of i) interleukin-2 (IL-2) and ii) an interleukin 1 (IL-1) inhibitor, wherein the IL-1 inhibitor is a recombinant IL-1Rα.

2. The method of claim 1, wherein the recombinant IL-1Rα is anakinra.

3. The method of claim 1, wherein the IL-2 is administered at a dose of 3.5 MIU/day or less.

4. The method of claim 3, wherein the IL-2 is administered between 0.5 and 1.5 MIU/day.

5. The method of claim 1, wherein the subject is a human patient having an auto-immune and/or inflammatory disorder selected from the group consisting of systemic lupus erythematosus, type I diabetes, HCV-related vasculitis, uveitis, myositis, systemic vasculitis, psoriasis, allergy, asthma, Crohn's disease, multiple sclerosis, rheumatoid arthritis, atherosclerosis, autoimmune thyroid disease, auto-inflammatory diseases, neuro-degenerative diseases, Alzheimer's disease, graft-versus-host disease, spontaneous abortion and allograft rejection; solid organ transplantation rejection, vasculitis, inflammatory bowel disease (IBD), allergic asthma, spondyloarthritis or ankylosing Spondylitis, Sjogren's syndrome, Systemic sclerosis, Alopecia aerate, and Ulcerative Colitis.

6. The method of claim 1, wherein the IL-2 is administered sequentially with the IL-1 inhibitor.

7. The method of claim 1, wherein the IL-2 is administered simultaneously with the IL-1 inhibitor.

8. The method of claim 7, wherein the IL-2 and the IL-1 inhibitor are administered within the same composition.

9. The method of claim 8, wherein the IL-2 and the IL-1 inhibitor are administered subcutaneously.

10. The method of claim 1, wherein the IL-2 comprises a fusion protein.

11. The method of claim 10, wherein the fusion protein comprises an IL-2 moiety and a moiety selected from the group consisting of an immunoglobulin or an immunoglobulin fragment, serum albumin, transferrin, and Fn3, or a variant thereof.

12. The method of claim 1, wherein the IL-2 comprises an IL-2 moiety conjugated to a non-protein polymer.

13. The method of claim 12, wherein the non-protein polymer is polyethylene glycol.

14. The method of claim 1, wherein the IL-2 is human IL-2 or an active analogue thereof, wherein the active analogue is aldesleukin.

15. The method of claim 14, wherein the IL-2 is human wild-type IL-2.

16. The method of claim 14, wherein the IL-2 is aldesleukin.

17. The method of claim 1, wherein the subject is a human subject.

* * * * *

SEQUENCE LISTING

<160> NUMBER OF SEQ ID NOS: 2

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 2
<211> LENGTH: 132
<212> TYPE: PRT
<213> ORGANISM: Artificial Sequence
<220> FEATURE:
<223> OTHER INFORMATION: aldesleukin

<400> SEQUENCE: 2

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Lys Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130